(12) United States Patent
Fischell et al.

(10) Patent No.: US 7,338,519 B2
(45) Date of Patent: Mar. 4, 2008

(54) STENT WITH OPTIMAL STRENGTH AND RADIOPACITY CHARACTERISTICS

(75) Inventors: Robert E. Fischell, Dayton, MD (US); David R. Fischell, Fair Haven, NJ (US); Janet Burpee, Fair Haven, NJ (US)

(73) Assignee: Cordis Corporation, Warren, NJ (US)

( * ) Notice: Subject to any disclaimer, the term of this patent is extended or adjusted under 35 U.S.C. 154(b) by 378 days.

(21) Appl. No.: 10/717,470

(22) Filed: Nov. 21, 2003

(65) Prior Publication Data

US 2004/0102836 A1  May 27, 2004

Related U.S. Application Data

(62) Division of application No. 09/899,142, filed on Jul. 6, 2001, now Pat. No. 6,699,278.

(60) Provisional application No. 60/234,497, filed on Sep. 22, 2000.

(51) Int. Cl.
*A61F 2/06* (2006.01)
(52) U.S. Cl. ..................................... 623/1.15
(58) Field of Classification Search ...................... None
See application file for complete search history.

(56) References Cited

U.S. PATENT DOCUMENTS

| | | |
|---|---|---|
| 3,657,744 A | 4/1972 | Ersek |
| 4,441,216 A | 4/1984 | Ionescu et al. |
| 4,503,569 A | 3/1985 | Dotter |
| 4,553,545 A | 11/1985 | Maass et al. |
| 4,580,568 A | 4/1986 | Gianturco |
| 4,733,665 A | 3/1988 | Palmaz |
| 4,776,337 A | 10/1988 | Palmaz |
| 4,800,882 A | 1/1989 | Gianturco |
| 4,856,516 A | 8/1989 | Hillstead |
| 4,886,062 A | 12/1989 | Wiktor |
| 4,907,336 A | 3/1990 | Gianturco |
| 4,969,458 A | 11/1990 | Wiktor |
| 4,990,131 A | 2/1991 | Dardik et al. |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco et al. |

(Continued)

FOREIGN PATENT DOCUMENTS

DE  32 05 942 A1  9/1983

(Continued)

*Primary Examiner*—Corrine McDermott
*Assistant Examiner*—Christopher Daniel Prone
(74) *Attorney, Agent, or Firm*—Rosenberg, Klein & Lee

(57) ABSTRACT

A stent in the form of a thin-walled, multi-cellular tubular structure is provided. The tubular structure has a longitudinal axis and the stent includes a plurality of circumferential sets of strut members. Each set of the strut members is longitudinally displaced from each other and connected to each other by longitudinally extending links. Each set of the strut members forms a closed and cylindrical portion of the stent. Further, each set of the strut members includes a plurality of connected curve sections and diagonal sections. The sets of the strut members further include end sets of strut members located at each end of the stent and central sets of strut members located between the end sets of the strut members.

4 Claims, 10 Drawing Sheets

U.S. PATENT DOCUMENTS

| | | | |
|---|---|---|---|
| 5,041,126 A | 8/1991 | Gianturco | |
| 5,064,435 A | 11/1991 | Porter | |
| 5,102,417 A | 4/1992 | Palmaz | |
| 5,104,404 A | 4/1992 | Wolff | |
| 5,116,365 A | 5/1992 | Hillstead | |
| 5,122,154 A | 6/1992 | Rhodes | |
| 5,131,908 A | 7/1992 | Dardik et al. | |
| 5,133,732 A | 7/1992 | Wiktor | |
| 5,135,536 A | 8/1992 | Hillstead | |
| 5,163,958 A | 11/1992 | Pinchuk | |
| 5,171,262 A | 12/1992 | MacGregor | |
| 5,176,660 A | 1/1993 | Truckai | |
| 5,178,618 A | 1/1993 | Kandarpa | |
| 5,192,307 A | 3/1993 | Wall | |
| 5,195,984 A | 3/1993 | Schatz | |
| 5,217,483 A | 6/1993 | Tower | |
| 5,222,971 A | 6/1993 | Willard et al. | |
| 5,246,445 A | 9/1993 | Yachia et al. | |
| 5,258,021 A | 11/1993 | Duran | |
| 5,266,073 A | 11/1993 | Wall | |
| 5,275,622 A | 1/1994 | Lazarus et al. | |
| 5,282,823 A | 2/1994 | Schwartz et al. | |
| 5,282,824 A | 2/1994 | Gianturco | |
| 5,290,305 A | 3/1994 | Inoue | |
| 5,292,331 A | 3/1994 | Boneau | |
| 5,304,200 A | 4/1994 | Spaulding | |
| 5,313,444 A | 5/1994 | Gianturco | |
| 5,314,472 A | 5/1994 | Fontaine | |
| 5,334,301 A | 8/1994 | Heinke et al. | |
| 5,342,348 A | 8/1994 | Kaplan | |
| 5,342,387 A | 8/1994 | Summers | |
| 5,354,257 A | 10/1994 | Roubin et al. | |
| 5,354,308 A | 10/1994 | Simon et al. | |
| 5,366,504 A | 11/1994 | Andersen et al. | |
| 5,370,683 A | 12/1994 | Fontaine | |
| 5,370,691 A | 12/1994 | Samson | |
| 5,375,612 A | 12/1994 | Cottenceau et al. | |
| 5,376,112 A | 12/1994 | Duran | |
| 5,382,261 A | 1/1995 | Palmaz | |
| 5,387,235 A | 2/1995 | Chuter | |
| 5,389,106 A | 2/1995 | Tower | |
| 5,395,390 A | 3/1995 | Simon et al. | |
| 5,397,355 A | 3/1995 | Marin et al. | |
| 5,403,341 A | 4/1995 | Solar | |
| 5,405,377 A | 4/1995 | Cragg | |
| 5,411,549 A | 5/1995 | Peters | |
| D359,802 S | 6/1995 | Fontaine | |
| 5,421,955 A | 6/1995 | Lau et al. | |
| 5,423,885 A | 6/1995 | Williams | |
| 5,441,515 A | 8/1995 | Khosravi et al. | |
| 5,441,516 A | 8/1995 | Wang et al. | |
| 5,443,477 A | 8/1995 | Marin et al. | |
| 5,443,496 A | 8/1995 | Schwartz et al. | |
| 5,443,498 A | 8/1995 | Fontaine | |
| 5,443,500 A | 8/1995 | Sigwart | |
| 5,449,372 A | 9/1995 | Schmaltz et al. | |
| 5,449,373 A | 9/1995 | Pinchasik et al. | |
| 5,449,382 A | 9/1995 | Dayton | |
| 5,496,365 A | 3/1996 | Sgro | |
| 5,527,354 A | 6/1996 | Fontaine et al. | |
| 5,569,295 A | 10/1996 | Lam | |
| 5,591,197 A | 1/1997 | Orth et al. | |
| 5,609,629 A * | 3/1997 | Fearnot et al. | 623/1.42 |
| 5,632,763 A | 5/1997 | Glastra | |
| 5,643,312 A | 7/1997 | Fischell et al. | |
| 5,649,952 A | 7/1997 | Lam | |
| 5,653,747 A | 8/1997 | Dereume | |
| 5,669,924 A | 9/1997 | Shaknovich | |
| 5,697,971 A | 12/1997 | Fischell et al. | |
| 5,725,572 A * | 3/1998 | Lam et al. | 623/1.16 |
| 5,755,734 A | 5/1998 | Richter et al. | |
| 5,800,508 A | 9/1998 | Goicoechea et al. | |
| 5,824,049 A | 10/1998 | Ragheb et al. | |
| 5,827,321 A * | 10/1998 | Roubin et al. | 623/1.16 |
| 5,861,027 A | 1/1999 | Trapp | |
| 5,876,449 A | 3/1999 | Starck et al. | |
| 5,911,754 A | 6/1999 | Kanesaka et al. | |
| 5,913,895 A | 6/1999 | Burpee et al. | |
| 5,935,162 A | 8/1999 | Dang | |
| 6,190,403 B1 * | 2/2001 | Fischell et al. | 623/1.16 |
| 6,231,598 B1 | 5/2001 | Berry et al. | |

FOREIGN PATENT DOCUMENTS

| | | |
|---|---|---|
| EP | 0 540 290 A2 | 5/1993 |
| EP | 0 540 290 A3 | 5/1993 |
| EP | 0 800 801 A1 | 10/1997 |
| EP | 0 824 900 A2 | 2/1998 |
| EP | 0 830 853 A1 | 3/1998 |
| EP | 0 734 698 B1 | 8/1998 |
| EP | 0 916 317 A1 | 5/1999 |
| FR | 566 807 | 2/1924 |
| GB | 0 662 307 A2 | 5/1951 |
| GB | 1 205 743 / A5 R | 9/1970 |
| WO | WO 96/26689 A1 | 9/1996 |
| WO | WO 96/34580 A1 | 11/1996 |
| WO | WO 97/25000 A1 | 7/1997 |
| WO | WO 98/19628 A1 | 5/1998 |
| WO | WO0053122 | 9/2000 |
| WO | WO 01/00112 A1 | 1/2001 |

* cited by examiner

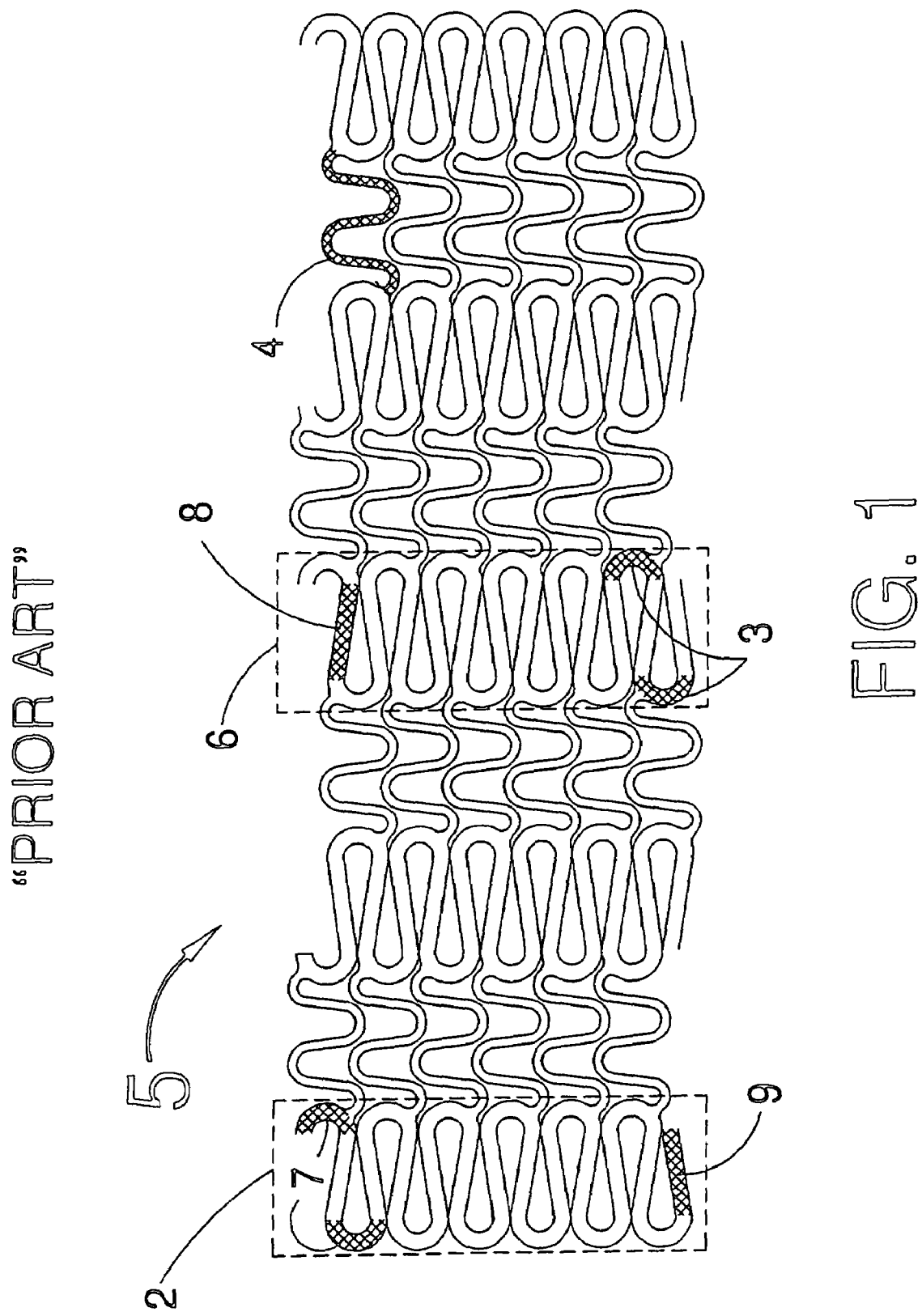

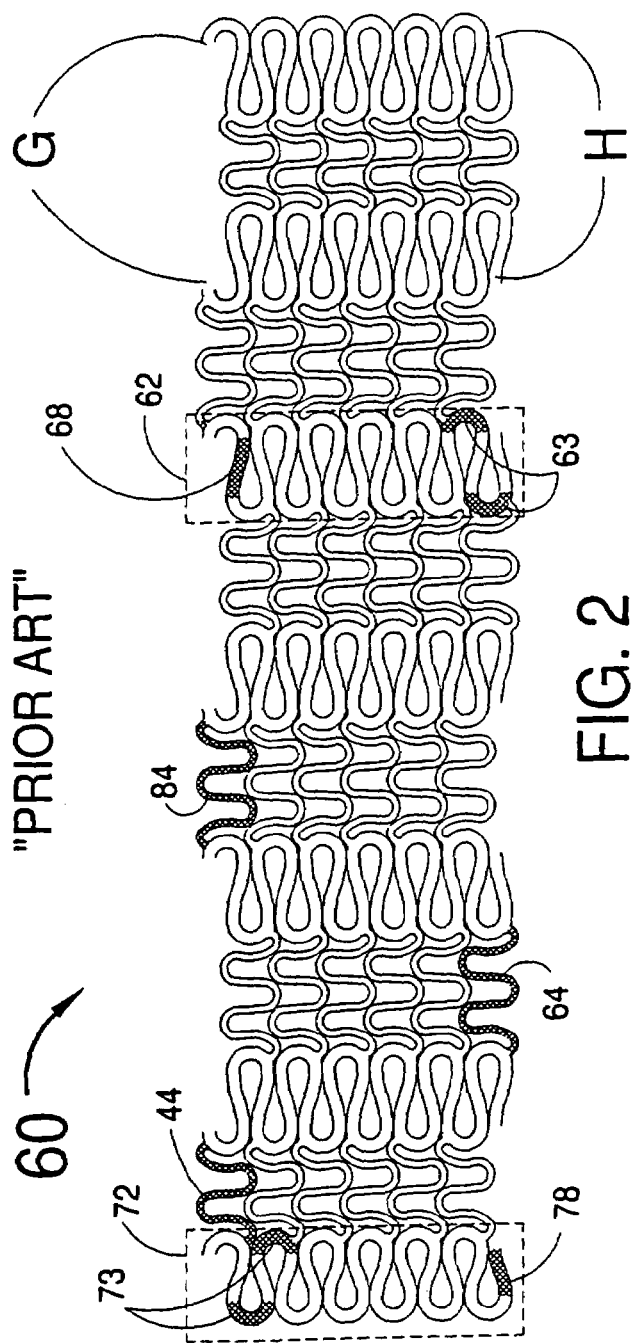
FIG. 2 "PRIOR ART"
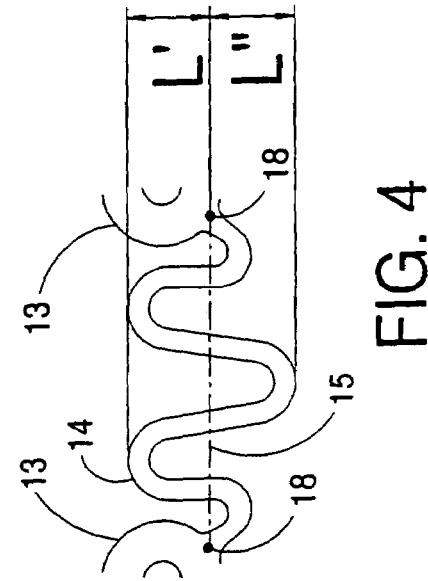
FIG. 4
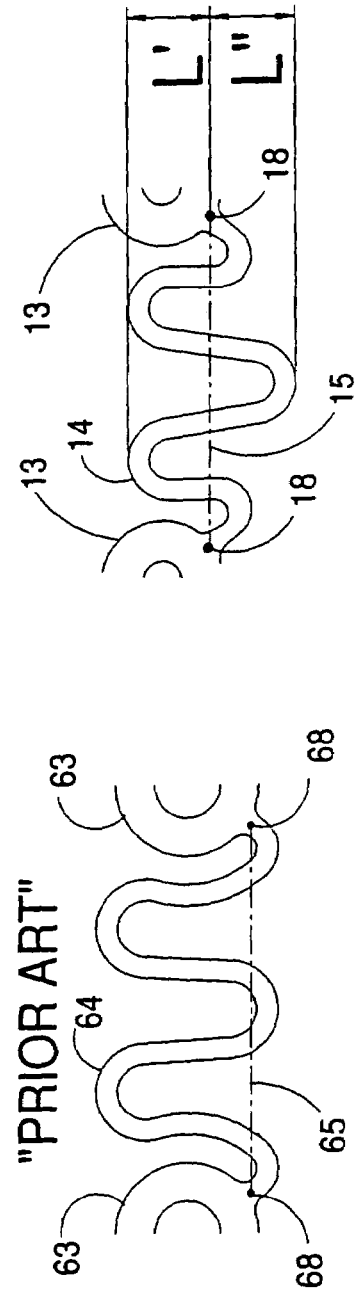
FIG. 3 "PRIOR ART"

STENT WITH OPTIMAL STRENGTH AND RADIOPACITY CHARACTERISTICS

This application claims the benefit of U.S. Provisional Application(s) No(s).: APPLICATION No(S).: 60/234,497 Sep. 22, 2000

This application is a divisional of application(s) application Ser. No. 09/899,142 filed on Jul. 6, 2001 now U.S. Pat. No. 6,699,278.

FIELD OF USE

This invention is in the field of stents for implantation into a vessel of a human body.

BACKGROUND OF THE INVENTION

Stents are well known medical devices that are used for maintaining the patency of a large variety of vessels of the human body. A more frequent use is for implantation into the coronary vasculature. Although stents have been used for this purpose for more than ten years, and some current stent designs such as the CORDIS BX Velocity® stent, Cordis Corporation, Miami Lakes, Fla., have the required flexibility and radial rigidity to provide an excellent clinical result, they are not always clearly seen under standard fluoroscopy.

Many current tubular stents use a multiplicity of circumferential sets of strut members connected by either straight longitudinal connecting links or undulating longitudinal connecting links. The circumferential sets of strut members are typically formed from a series of diagonal sections connected to curved sections forming a closed-ring, zig-zag structure. This structure opens up as the stent expands to form the element in the stent that provides structural support for the arterial wall. A single strut member can be thought of as a diagonal section connected to a curved section within one of the circumferential sets of strut members. In current stent designs such as the BX Velocity® stent, these sets of strut members are formed from a single piece of metal having a uniform wall thickness and generally uniform strut width. Although a stent with uniform width of the strut members will function, if the width is increased to add strength or radiopacity, the sets of strut members will experience increased strain upon expansion. High strain can cause cracking of the metal and potential fatigue failure of the stent under the cyclic stress of a beating heart.

Existing highly radiopaque stents, such as the gold plated NIROYAL stent sold by Boston Scientific, Inc., Natick Mass., can obscure the inside of the vessel due to the high radiopacity over the entire length of the stent. The BeStent sold by Medtronic, Inc., Minneapolis MN, has small gold markers at the ends of the stent. Those markers only mark an end point without allowing visualization of the entire end set of strut members.

Fischell et al, in U.S. Pat. No. 6,086,604, discloses a stent with the end sets of strut members being gold plated. Such a stent would have ideal radiopacity but may be subject to the corrosive effects incurred through placement of dissimilar metals in an electrolytic solution such as blood. There has also been significant evidence that gold is a poor surface material for stents because it may increase the risk of subacute thrombosis or restenosis. Further, Fischell et al, in U.S. Pat. No. 5,697,971 discloses in its FIG. 7, a stainless steel stent with increased width diagonal sections in all the circumferential sets of strut members.

SUMMARY OF THE INVENTION

An ideally radiopaque stent would have end sets of strut members that are highly radiopaque so that they can be readily seen, even using low power fluoroscopy, and would further contain a central section that is visible but not too bright so as to obscure the lumen when high power fine film angiograms are taken. The stent should also have only one material on its outside surface to avoid potential corrosion; that material should not promote subacute thrombosis or restenosis.

The present invention is a stent that is designed to have optimal strength and radiopacity with good biocompatibility. Unfortunately, the choices of appropriate biocompatible metals available as thin wall tubing for stent construction are somewhat limited. To achieve optimal radiopacity, the stent design of the present invention is adjusted to the specific radiopacity and strength characteristics of the metal from which the stent is fabricated. What is more, coatings such as parylene may be needed to avoid corrosion from stents with less biocompatible materials and/or dissimilar metals on the stent's outer surface. Of extreme importance to the present invention is the achievement of optimal radiopacity in a stent that ideally is only 0.004 inches wall thickness or less. Such a stent would have a pre-deployment outer diameter (profile) that would be at least 0.003 inches less than currently marketed stents. Ideally, the stent described herein would have a wall thickness between 0.0025 inches and 0.004 inches.

Described herein are the novel design elements for stents formed from the following materials:
1. A highly radiopaque metal such as tantalum;
2. Metals somewhat more radiopaque than stainless steel, such as the cobalt based alloy L605;
3. Stents coated or plated with highly radiopaque materials like gold; and
4. Layered materials such as alternative layers of tantalum and stainless steel.
5. The novel design elements that are described herein include:
1. Tapered strut width for stents formed from highly radiopaque metals. Although reducing the width of the longitudinally diagonal section alone will reduce radiopacity without significantly affecting radial strength, by having a taper on the curved sections of the circumferential sets of strut members, a greatly reduced level of strain upon stent expansion can be achieved without sacrificing radial strength. This is extremely important, as it allows a stent to be made much stronger than a stent with uniform width of the strut members while staying within the same strain limit for the material.

Tantalum is a metal that has been used in stents; which metal is highly radiopaque. The optimal radiopacity for a stent design using tantalum could have uniform width for the circumferential sets of strut members and a wall thickness of about 0.0025 inches. To provide more radial strength and to reduce the probability of the stent ends flaring out during deployment, a wall thickness of about 0.003 inches to 0.035 inches would be highly desirable. With uniform width sets of strut members, a 0.035 inches wall thickness tantalum stent would be too bright under cine angiography. To reduce the radiopacity of the design without significantly impacting the radial strength of the deployed stent, the present invention envisions curved sections and diagonal sections, either or both of which could have a variable or tapered width. The curved sections should be tapered (wider at the center compared to the ends) to reduce strain as previously described. The longitudinally diagonal sections can be thinner in the center than at the ends, to reduce radiopacity for the central sets of strut members.

It is envisioned that the novel stent described herein might have wider diagonal sections for the end sets of strut members as compared to the central sets of strut members. This feature would enhance the radiopacity of the end sets of strut members while retaining a moderate level of radiopacity for the central sets of strut members. It is also envisioned to have both reduced width diagonals and/or reduced wall thickness for the central sets of strut members. It should be remembered that it is fluoroscopic visualization of the end sets of strut members that is most important for visualizing stents placed inside a coronary artery.

2. Thicker diagonal sections for metals with radiopacity slightly better than stainless steel. The cobalt/tungsten alloy L605 is a stronger and more radiopaque metal compared to stainless steel. To achieve optimal radiopacity using L605 with uniform width sets of strut members, the wall thickness is optimally equal to or greater than 0.0045 inches. To provide optimal radiopacity with such a metal in stents of wall thickness 0.004 inches or less, the present invention envisions wider diagonal sections in the sets of strut members. Thus, the tapered diagonal sections would be wider than the curved sections. The tapered curved section design for reduced strain may also be highly desirable for stents made from the L605 alloy.

3. End sets of strut members with thinner curved sections. Stent deliverability into curved coronary arteries is improved when the diagonal sections of the end sets of strut members have a decreased length as compared to the length of the diagonal sections of the central sets of strut members. A shorter length of the diagonal sections will also reduce outward flaring upon expansion of the stent. Decreasing end flaring of the deployed stent is of particular importance for stents having very thin walls.

Previous designs that describe a stent with shorter diagonal sections in the end sets of strut members are limited by the strain limit allowed for the end sets of strut members. As a result, if the end sets of strut members are made as strong as possible while being limited by the maximum allowable strain for that metal, the central sets of strut members will not have optimized radial strength. The present invention envisions optimizing the radial strength for all sets of strut members, i.e., the metal in all sets of strut members just reach the maximum allowable strain at the limiting diameter for the stent's expansion. To achieve this desired attribute, the stent described herein has the curved sections of the end sets of strut members being less wide than the curved sections of the central sets of strut members.

4. Good side branch arterial access while maintaining small cell size. The stents described herein are typically closed cell stents, having a curved section of a central set of strut members connected to an adjacent set of strut members by a longitudinally extending link. In one embodiment of the present invention, the circumferential sets of strut members are joined by undulating longitudinal connecting links with each link having a multiplicity of curved segments so as to increase the perimeter of the stent's closed cells. One aspect of the present invention is that the perimeter of each of the stent's closed cells should be at least 9 mm long. This design parameter allows each cell of the stent to be expanded to a circular diameter of approximately 3 mm (i.e., 9/$\pi$ mm~3 mm). This feature allows the "unjailing" of side branches of the artery into which the stent is placed. The ideal design to be radially strong, prevent plaque prolapse and still allow sidebranch access will have a maximum deployed cell area of less than 0.005 in.$^2$ while having a cell perimeter that is at least 9 mm in length, so as to allow unjailing of side branches. A good cell for side branch access should have a perimeter length between 9 mm and 11 mm. (i.e. an expandable circular diameter between 2.86 mm and 3.5 mm). Cell perimeters between 9.5 and 10 mm are optimal.

5. Flexible undulating longitudinal links with good support between adjacent sets of strut members. To provide a strong bridge connection between adjacent circumferential sets of strut members, the flexible undulating longitudinal connecting links should have nearly equal extension in the circumferential direction on each side of a line drawn between the attachment points of the flexible undulating longitudinal connecting link to the curved sections of adjacent sets of strut members. "N" and inverted "N" shapes for the connecting links inherently have equal circumferential displacement on each side of the line connecting their attachment points. The specially designed "M" or "W" shapes of the present invention also provide this desirable attribute. Nearly equal circumferential lengths on either side of a line drawn between the attachment points of the flexible undulating longitudinal connecting links help in preventing plaque from pushing the "M" or "W" shaped link inward into the lumen of the stent when the stent is deployed into an artery.

The "M" and "W" shapes are of particular advantage in obtaining the desired attribute of small area cells that have good side branch access capability because of an increased perimeter length. It should also be understood that the "M" and "W" shapes each add an additional half cycle of undulating link length to the cell perimeter as compared to an "N" shaped link design, thus improving the stent's longitudinal flexibility. It should also be noted that a "W" link is simply an inverted "M" link.

6. Variable thickness radiopaque coatings. The NIROYAL™ stent has a uniform thickness of gold plating, which makes the center too radiopaque as compared to the radiopacity of the end sets of strut members. Fischell et al., U.S. Pat. No. 6,086,604, teaches stents having gold placed at the end sets of strut members. This creates a potential for corrosion from dissimilar metals, namely, gold and stainless steel. The present invention envisions a gold coating that is sufficiently thick on the end sets of strut members to provide optimal radiopacity with a thin coating of gold on the rest of the stent. This design prevents obscuring of the arterial lumen while providing an exterior surface for the stent that is a single metal, thus avoiding electrolytic corrosion.

7. Polymer coatings for stents coated with gold or having dissimilar metal surfaces. For stents with non-biocompatible or dissimilar metals, the present invention envisions the use of a polymer such as parylene to coat the entire outer surface of the stent. This would improve biocompatibility and also allow attachment of organic compounds such as heparin or phosphorylcholine for reduced thrombogenicity or drugs, such as taxol or rapamycin, for reduced cell proliferation and a decreased rate of restenosis. It is also known that highly radiopaque materials like tungsten can be mixed into polymers. A stent coating including a plastic with mixed in radiopaque metal could be used to enhance both radiopacity and biocompatibility. Such a polymer coating could also be advantageous with a gold coated stent.

8. Providing a variable wall thickness. The present invention also envisions next generation manufacturing techniques using photo-etching, whereby a stent pattern is etched into a thin-walled metal tube. These techniques already can produce variations in wall thickness as well as strut width for any stent pattern. The present invention envisions use of these techniques to create stents with optimal radiopacity. In particular for a stent formed from a single metal or alloy, thicker metal at each end of the stent could increase radiopacity there as compared to the central section of the stent. Perhaps more important is the use of multi-thickness etching techniques with a two- or three-layered tube where one of the layers is a highly radiopaque material such as tantalum. For example, a two-layer tube having one layer of stainless steel and a second layer of tantalum could be etched to provide the end sets of strut members with 0.001 inches of tantalum and 0.0025 inches of stainless steel while the remainder of the stent would have less than 0.0005 inches of tantalum with a stainless steel layer of 0.003 inches. It is also envisioned that there could be tantalum only on the end sets of strut members. Thus, one could produce a stent with enhanced radiopacity at the ends with the stent having a uniform wall thickness.

One could even have a stent with increased wall thickness of a metal at the central region of the stent but still having a decreased radiopacity at that central region if, for example, the stent had tantalum end struts with stainless steel center struts. Such a stent would be strongest in the center where the thickest plaque must be restrained.

It is also envisioned that any of the above optimal radiopacity stent designs may be used with plastic coatings such as parylene, antithrombogenic coatings such as heparin or phosphorylcholine, or anti-proliferative coatings such as taxol or rapamycin.

Thus it is an object of the present invention to have a stent with tapered curved sections, the center of the curved sections being wider than ends of the curved sections so as to reduce plastic strain as the stent is expanded as compared to a curved section with uniform width.

Another object of the present invention is to have a stent with tapered diagonal sections in the sets of strut members where the center of the diagonal section is narrower than the ends to reduce the radiopacity of central sets of strut members of the stent as compared to a stent with diagonal sections having a uniform width.

Still another object of the invention is to have a stent with decreased wall thickness at the central struts compared to the end struts so as to have a comparatively higher radiopacity for the end sets of strut members.

Still another object of the present invention is to have a stent with tapered diagonal sections for one or more of the sets of strut members where the center of the diagonal section is wider than the ends to increase the radiopacity of the end sets of strut members as compared to a stent with uniform width of the diagonal sections.

Still another object of the present invention is to have end sets of strut members having both shorter diagonal sections and thinner width curved sections as compared to those sections in the central sets of strut members.

Still another object of the present invention is to have a tantalum stent with wall thickness less than 0.035 inches having tapered sets of strut members whereby the diagonal sections are less wide than the width at the center of the curved sections.

Still another object of the present invention is to have a closed cell stent design with maximum post-deployment cell area less than 0.005 square inches and a cell perimeter length that is equal to or greater than 9 mm.

Still another object of the present invention is to have a stent with a radiopaque metal coating where the radiopaque metal coating has greater wall thickness on the end sets of strut members as compared to thickness on the sets of strut members at the center of the stent.

Still another object of the present invention is to have a stent etched from a multi-layer metal tube having one layer significantly more radiopaque than at least one other layer; the etched stent being formed with increased wall thickness of the more radiopaque layer on the end sets of strut members as compared with the sets of strut members at the center of the stent.

Still another object of the present invention is to have a closed cell stent design with "M") or "W" shaped flexible undulating longitudinal connecting links wherein the circumferential extent of the flexible undulating longitudinal connecting links is approximately equal on each side of a line drawn between the proximal and distal attachment points of the flexible undulating longitudinal connecting link.

Still another object of the present invention is to have the stent with optimized radiopacity formed with an outer surface that is plastic coated to improve biocompatibility.

Still another object of the present invention is to have the stent with optimized radiopacity that is coated with a plastic material and an additional organic compound to prevent thrombus formation and/or restenosis.

Still another object of the present invention is to have a stent coated with a plastic material that includes a radiopaque filler material.

These and other objects and advantages of this invention will become apparent to the person of ordinary skill in this art field upon reading of the detailed description of this invention including the associated drawings.

BRIEF DESCRIPTION OF THE DRAWINGS

FIG. 1 is a flat layout of a prior art stent having uniform strut width for the circumferential sets of strut members.

FIG. 2 is a flat layout of a prior art stent design having "M" and "W" flexible connecting links.

FIG. 3 is an enlargement of the "M" link of the stent design of FIG. 2.

FIG. 4 is an enlargement of the improved "M" link design of the present invention.

DETAILED DESCRIPTION OF THE DRAWINGS

Figure 5:
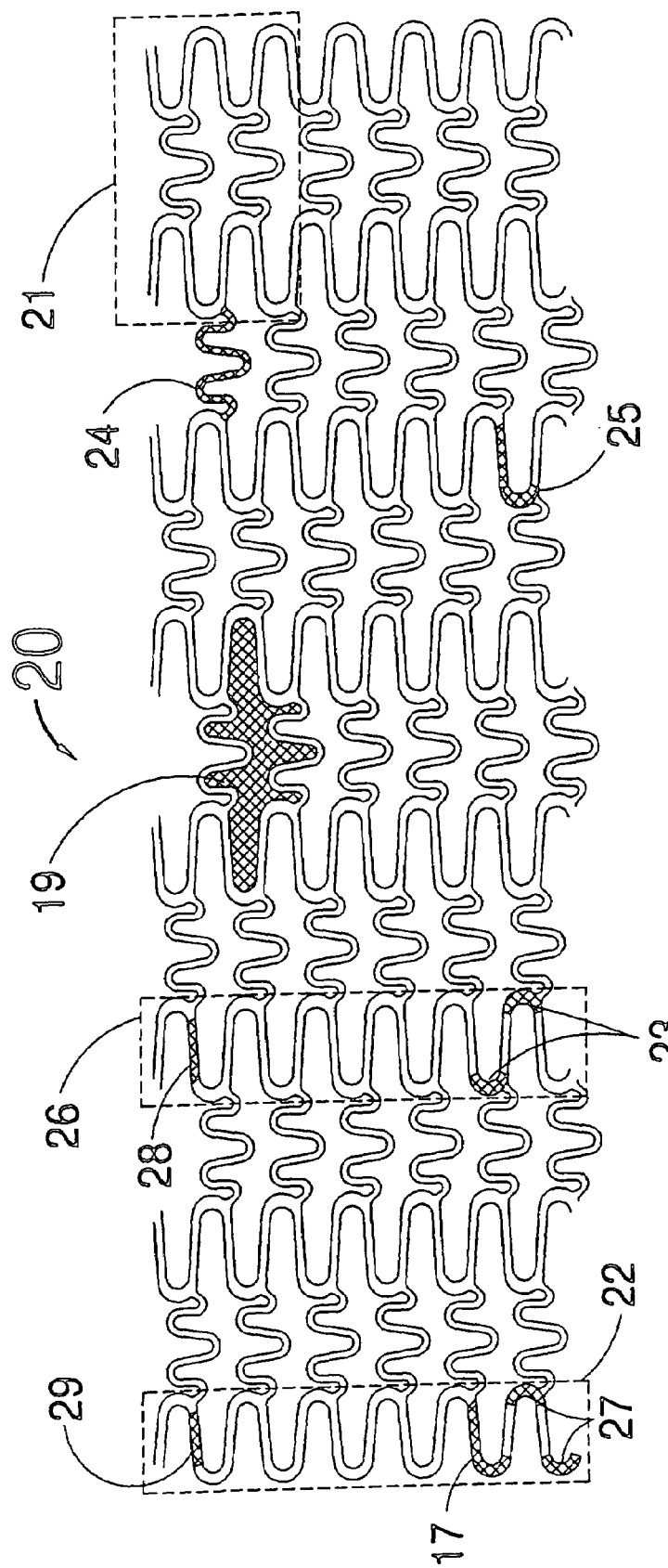
FIG. 5 is a flat layout of the present invention stent design for a highly radiopaque metal.

FIG. 1 shows a flat layout of an embodiment of a prior art stent described by Fischell et al in U.S. Pat. No. 6,190,403. The stent 5 of FIG. 1 is shown in its crimped, pre-deployed state as it would appear if it were cut longitudinally and then laid out into a flat, 2-dimensional configuration. The stent 5 comprises end sets of strut members 2 located at each end of the stent 5 and three central sets of strut members 6 connected each to the other by sets of longitudinally extending undulating "N" links 4. The end sets of strut members 2 consist of alternating curved sections 7 and diagonal sections 9. The central sets of strut members 6 located longitudinally between the end sets of strut members 2 consist of alternating curved sections 3 and diagonal sections 8. In the prior art stent 5, the longitudinally diagonal sections 9 of the end sets of strut members 2 are shorter in length than the longitudinally diagonal sections 8 of the central sets of strut members 6. The shorter diagonal sections 9 will reduce the stiff longitudinal length of metal at the ends of the stent 5 to improve deliverability (by reducing "fish-scaling") and will also increase the post-expansion strength. of the end sets of strut members 2 as compared with the central sets of strut members 6. In this prior art stent, the width of the curved sections 3 and 7 and the diagonal sections 8 and 9 are all the same. There is no variation in width within any set of strut members or between the end sets of strut members 2 and the central sets of strut members 6. The stent 5 is a design well suited to stainless steel having a wall thickness of 0.0045" or greater, such as found in the CORDIS BX Velocity® stent.

If the stent 5 were formed from a highly radiopaque metal such as tantalum with wall thickness of 0.0030 to 0.0035 inches and with sets of strut members 6 having widths of greater than the 0.005 inches that is necessary for good radial strength, then the stent would be too radiopaque. In addition, with a wall thickness of 0.003 inches or less, the end sets of strut members 2 might have a tendency to flare outwardly into the vessel wall upon expansion. If the end sets of strut members 2 are designed to be as strong as possible while not exceeding metal strain limits at the largest usable diameter of the stent 5, then the central sets of strut members 6 with longer diagonal sections 8 will not have maximized radial strength assuming the same strut width for both central sets of strut members 6 and end sets of strut members 2. Optimized strength at the longitudinal center of a stent is important as it is that region that must typically hold back a larger amount of plaque than at the ends of the stent.

One embodiment of the present invention provides that each set of strut members should have maximized radial strength rather than having the central sets of strut members 6 being less strong than the end sets of strut members as previously described. This design would be similar to the stent 5 of FIG. 1 with the novel improvement being that the width of the curved sections 3 of the central sets of strut members 6 would be greater than the width of the curved sections 7 of the end sets of strut members 2. The greater width of the curved sections 3 will increase the strength of the central sets of strut members 6 compensating for loss of radial strength because of the longer diagonal sections 8.

The stent 60 shown in FIG. 2 is a flat layout of a prior art stent design having "N", "M" and "W" flexible connecting links. The stent 60 is shown in its crimped pre-deployed state as it would appear if it were cut longitudinally and then laid out into a flat, 2-dimensional configuration. It should be clearly understood that the stent 60 is in fact cylindrical in shape, which cylindrical shape would be obtained by rolling the flat configuration of FIG. 2 into a cylinder with the top points "G" joined to the bottom points "H". The stent 60 is typically fabricated by laser machining of a cylindrical, stainless steel tube.

A central set of strut members 62 is a cylindrical, closed, ring-like section of the stent 60 consisting of a multiplicity of curved sections 63 connected to diagonal sections 68. Every curved section 63 of each central set of strut members 62 is attached to a connecting link which is either a flexible "N" link 44, "M" link 64 or a "W" link 84. The stent 60 also has two end sets of strut members 72 consisting of a multiplicity of curved sections 73 connected to diagonal sections 78. In this embodiment, half of the curved sections 73 of the end set of strut members 72 are attached to "N" links 44 with the other half of the curved sections 73 situated at the extreme ends of the stent 60. The diagonal sections 78 of the end sets of strut members 72 are shorter than the diagonal sections 68 of the central sets of strut members 62. Shorter diagonal sections enhance the post-expansion radial strength of the end sets of strut members 72 as compared to the central sets of strut members 62.

FIG. 3 is an enlargement of the "M" link 64 of the prior art stent of FIG. 2. One disadvantage of this design relates to the circumferential extent of the "M" link 64 with respect to a line 65 that could be drawn between the two attachment points 68 where the "M" link 64 attaches to the curved sections 63. Because almost all of the "M" link 64 lies above the line 65, pressure on the top of the "M" link 64 from plaque in an artery could bend the top of the "M" link 64 inward into the arterial lumen. This would be highly undesirable. Ideally, an "M" or "W" link should have an equal circumferential extent on either side of a line drawn between the attachment points to adjacent sets of strut members as shown in FIG. 4.

One aspect of the present invention is an improved "M" link 14 as shown in FIG. 4. The "M" link 14 has a circumferential extent (i.e., length) L' above and L" below the line 15. The line 15 is drawn between the attachment points 18 where the "M" link 14 attaches to adjacent curved sections 13. Such a balanced design would diminish any likelihood of the flexible connecting link 14 from expanding into the arterial lumen.

FIG. 5 is a flat layout view of a stent 20 that includes some embodiments of the present invention. The design of FIG. 5 is particularly applicable to stents made from a highly radiopaque metal such as tantalum. The stent 20 of FIG. 5 is shown in flat, layout view based on its pre-deployed state, as it would appear before it is crimped onto a balloon catheter. The stent 20 comprises end sets of strut members 22 located at each end of the stent 20 and central sets of strut members 26 connected each to the other by sets of individual flexible "M" links 24. The "M" links 24 are similar to the "M" link14 of FIG. 4. The end sets of strut members 22 consist of a multiplicity of curved sections 27 connected to diagonal sections 29. The central sets of strut members 26 located longitudinally between the end sets of strut members 22 consist of a multiplicity of curved sections 23 connected to diagonal sections 28.

One can also define a strut element 25 as being composed of one adjacent curved section 23 joined to a diagonal section 28. As seen in FIG. 5, it is clear that one can describe a central set of strut members 26 as being a closed, circumferential, ring-like structure comprising a multiplicity of connected strut elements 25. An end set of strut members could be likewise defined as being a multiplicity of connected strut elements 17.

The stent 20 is a closed cell stent having cells 19 formed from portions of adjacent sets of strut members connected by "M" links 24. For coronary arteries, prolapse of plaque into the arterial lumen will be minimized if the area within the cell 19 does not exceed 0.005 square inches at all diameters up to the maximum deployment diameter of the stent 20. An important aspect of stent design is to be able to place a guidewire through the expanded cell 19, into a side branch vessel. A balloon angioplasty catheter can then be advanced over the guidewire and inflated to enlarge and circularize the opening of the cell 19 to "unjail" the side branch vessel. By "unjailing" is meant removing metal from the ostium of the side branch vessel, thus improving blood flow to that side branch. One concept of the present invention is that the cell 19 has an interior length of the perimeter that is at least 9 mm. Since balloon dilatation of the cell 19 would cause it to be near circular, an inside perimeter length around inside of the cell 19 would provide an inside diameter of $9/\pi$, which is approximately 3 mm. A good cell design for side branch access should have an inside perimeter length between 9 mm and 11 mm. (i.e., an expanded inside circular diameter between 2.86 and 3.5 mm) where cell perimeters between 9.5 and 10 mm are optimal and would be suitable for essentially any side branch of a coronary artery.

In the stent 20, the diagonal sections 29 of the end sets of strut members 22 are shorter in length than the diagonal sections 28 of the central sets of strut members 26. The shorter diagonal sections 29 will reduce the longitudinal extent of the metal strut at the end of the stent to improve deliverability into a vessel of the human body by decreasing fish-scaling. In the stent 20, the width of the curved sections 23 and 27 and the diagonal sections 28 and 29 are different as compared to the prior art stents 5 and 6 of FIGS. 1 and 2.

Figure 6:
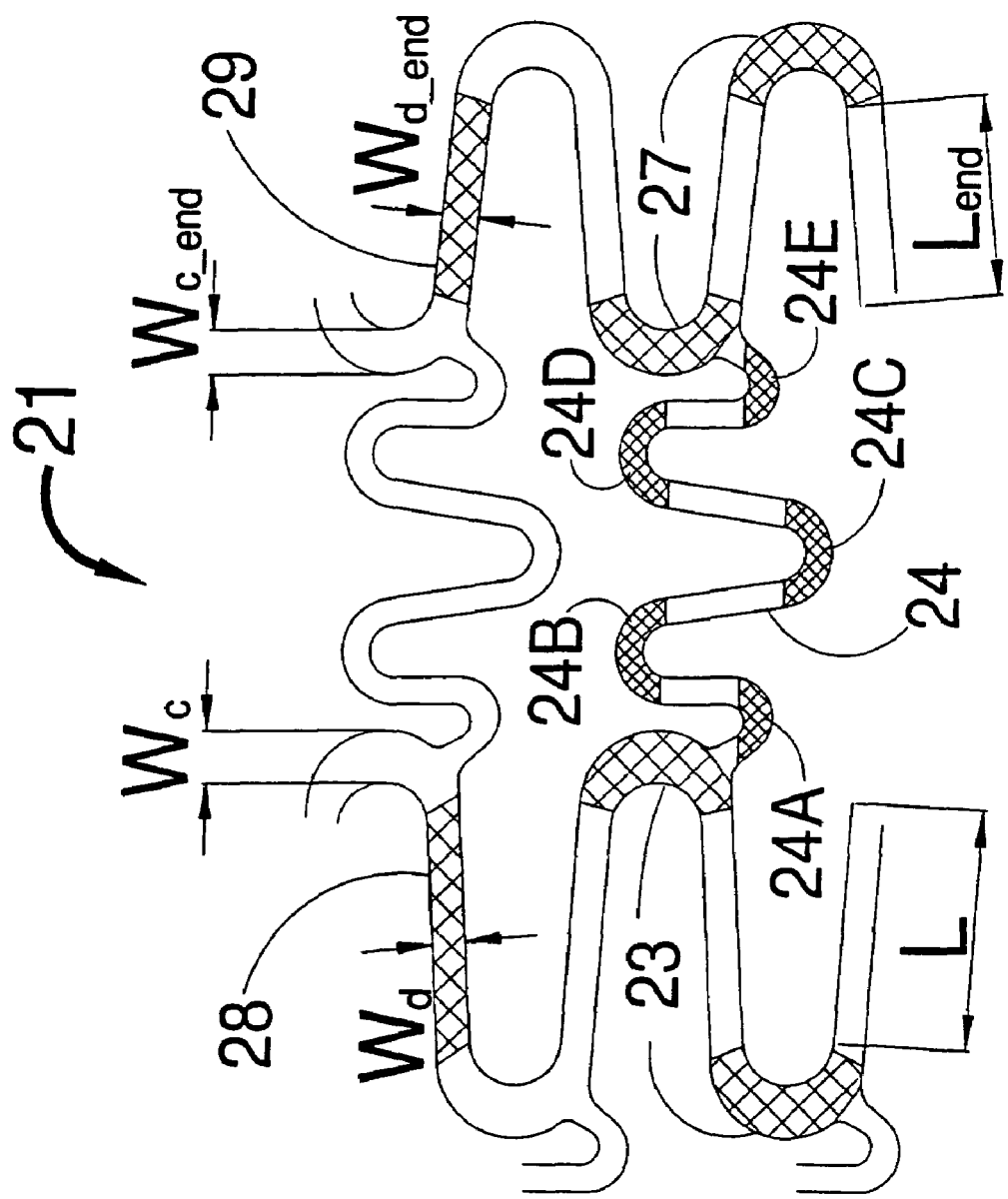
FIG. 6 is a flat layout of part of the present invention stent design of FIG. 5.

The exact design of the stent 20 is most clearly seen in the expanded view of the stent section 21 of FIG. 5 as shown enlarged in FIG. 6. FIG. 6 shows that the curved sections 23 (of the central sets of strut members 26 of FIG. 5) have a width at the center of the curve $W_c$. The width of the curved sections 23 taper down as one moves away from the center of the curve until a minimum width $W_d$ is reached at the center of the section 28. To achieve this taper, the inside arc of the curved section 23 has a center that is longitudinally displaced from the center of the outside arc. This tapered shape for the curved section 23 provides a significant reduction in metal strain with little effect on the radial strength of the expanded stent as compared to a stent having sets of strut members with a uniform strut width.

This reduced strain design has several advantages. First, it can allow the present invention design to have a much greater usable range of radial expansion as compared to a stent with a uniform strut width. Second, it can allow the width at the center of the curve to be increased which increases radial strength without greatly increasing the metal strain (i.e. one can make a stronger stent). Finally, the taper reduces the amount of metal in the stent and that should improve the stent thrombogenicity.

FIG. 6 also shows a unique design for the end sets of strut members 22. The diagonal sections of the end sets of strut members 22 have a length $L_{end}$ that is shorter than the length L of the diagonal sections 28 of the central sets of strut members 26. To maximize the radial strength of a stent along its entire length, each set of strut members should just reach the maximum allowable plastic strain for the metal being used at the largest allowable expanded diameter of the stent. In the stent of FIG. 1, the curved sections 7 of the end sets of strut members 2 and the curved sections 3 of the central sets of strut members 6 have the same widths. As a result, the end sets of strut members 2 (which have shorter diagonal sections 9) will reach the maximum allowable diameter at a level of strain that is greater than the level of strain experienced by the central sets of strut members 6.

An optimum strength stent design would have the same strain at the maximum stent diameter for both the end sets of strut members 2 and the central sets of strut members 6. For the stent design of FIGS. 5 and 6, one desires to have the end sets of strut members 22 reach the maximum strain limit at the same stent diameter as the central sets of strut members 26. The present invention teaches a design with the width at the center of the curve $W_{c\_end}$ of the curved section 27 being less than the width $W_c$ of the curved sections 23 of the central sets of strut members 26. This reduced width for the curved sections 23 compensates for the shorter length $L_{end}$ of the end diagonal sections 29 so that there is the same strain in both the central and end sets of strut members 22 and 26 respectively as the stent 20 is expanded to its maximum allowable diameter.

The end sets of strut members 22 can also be tapered like the central sets of strut members 26 where the width of the strut tapers down as one moves away from the center of the curve of the curved sections 27 until a minimum width $W_{d\_end}$ is reached at the diagonal section 29. The curved sections 23, 27 each have an inside (concave) arc and an outside (convex) arc. Each arc has a center that is longitudinally displaced from the other center.

The tapered strut design shown in FIGS. 5 and 6 also has an advantage for stents made from highly radiopaque metals such as tantalum. If one uses uniform strut width as seen with the stent 5 of FIG. 1, then a properly designed thin-walled (0.0025 inches to 0.035 inches) wall tantalum stent may be too radiopaque. The reduced metal from the thinner diagonal-sections 28 and 29 will decrease the radiopacity without affecting radial strength. Nominal dimensions and dimension ranges (all in inches) for a tantalum stent produced using the design of FIG. 5 are as follows:

| Element | Nominal | Range |
| --- | --- | --- |
| $W_c$ | 0.006 | 0.0045 to 0.007 |
| $W_d$ | 0.0045 | 0.035 to 0.005 |
| $W_{c\_end}$ | 0.0045 | 0.004 to 0.005 |
| $W_{d\_end}$ | 0.0045 | 0.035 to 0.005 |
| L | 0.028 | 0.020 to 0.030 |
| $L_{end}$ | 0.025 | 0.015 to 0.026 |
| Wall Thickness | 0.003 | 0.0025 to 0.035 |

Although the present invention shows the "M" shaped flexible link 24 being used, the present invention strut designs will function with any link shape including "N", "W", "S" "U", "V" and inverted "N", "U" and "V" designs. It should also be noted that the "M" link 24 shown in FIG. 6 has exactly five longitudinally extending curved segments 24A, 24B, 24C, 24D and 24E.

Figure 7:
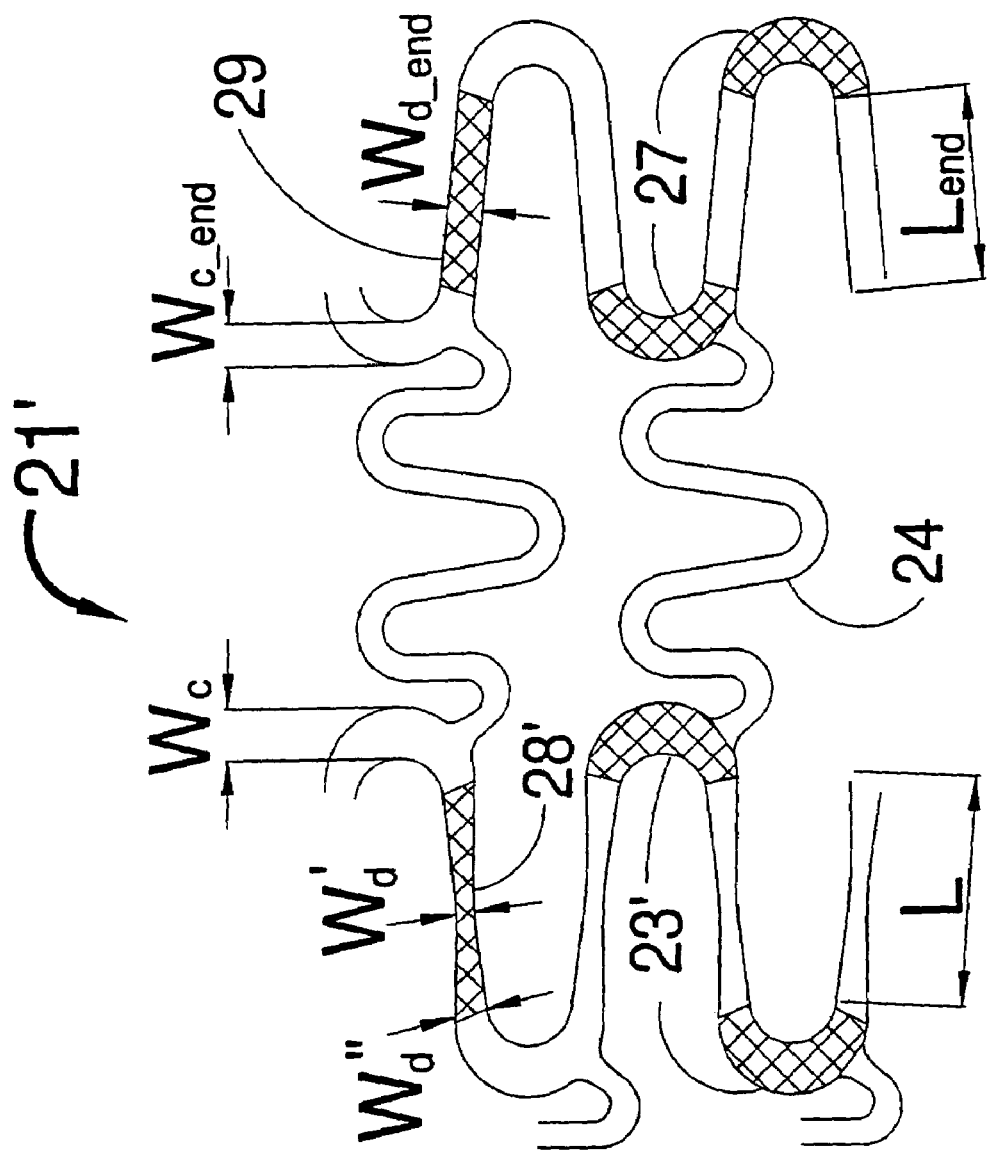
FIG. 7 is a flat layout of an alternate embodiment of part of the present invention stent design of FIG. 5.

FIG. 7 is an alternative embodiment 21' of section 21 shown in FIG. 6 of the present invention stent 20 of FIG. 5. In this embodiment, the only difference is the shape of the diagonal sections 28'. The diagonal sections 28 of FIG. 6 have uniform thickness. The diagonal sections 28' of FIG. 7 are tapered from a width $W_d''$ at the end of the diagonal section 28' where it connects to the curved sections 23' to a width $W_d'$ at the center of the diagonal section 28'. The advantage of the inward taper of the diagonal sections 28' is that removal of more metal will reduce the radiopacity of the longitudinal center region of the stent 20 as compared to a stent with uniform width diagonal sections 28 as seen in FIG. 6. The additional taper may also further reduce the metal strain as the stent is expanded. Although one could taper the diagonal sections 29 of the end sets of strut members 22 of FIG. 5, there is an advantage in having the end sets of strut members 22 being more radiopaque than the central sets of strut members 26. This is because visualization of the stent ends is the most important aspect of radiopacity for a stent. Therefore, a preferred embodiment of the present invention is as seen in FIG. 7 to have tapered diagonal sections 28' in the central sets of strut members 26 and uniform thickness diagonal sections 29 (having a greater average width) for the end sets of strut members 22.

Instead of connecting every curved section with a flexible link, an alternate embodiment may use straight links connecting only half of the curved sections of the sets of strut members. Such a stent could also have the advantage of a reduced strain strut design as shown in FIGS. 5, 6 and 7.

For the stent of FIG. 5, it should also be understood that the wall thickness of the central set of strut members 26 could be thinner that the wall thickness of the end set of strut members 22. Also it should be noted that the "M" links 24 also have a much narrower width as compared to the width of any strut member of the end set of strut members. Both these attributes of the stent 20 create the following desirable radiopacity characteristics: highly radiopaque end sets of strut members and decreased radiopacity at the central region of the stent 20.

Figure 8:
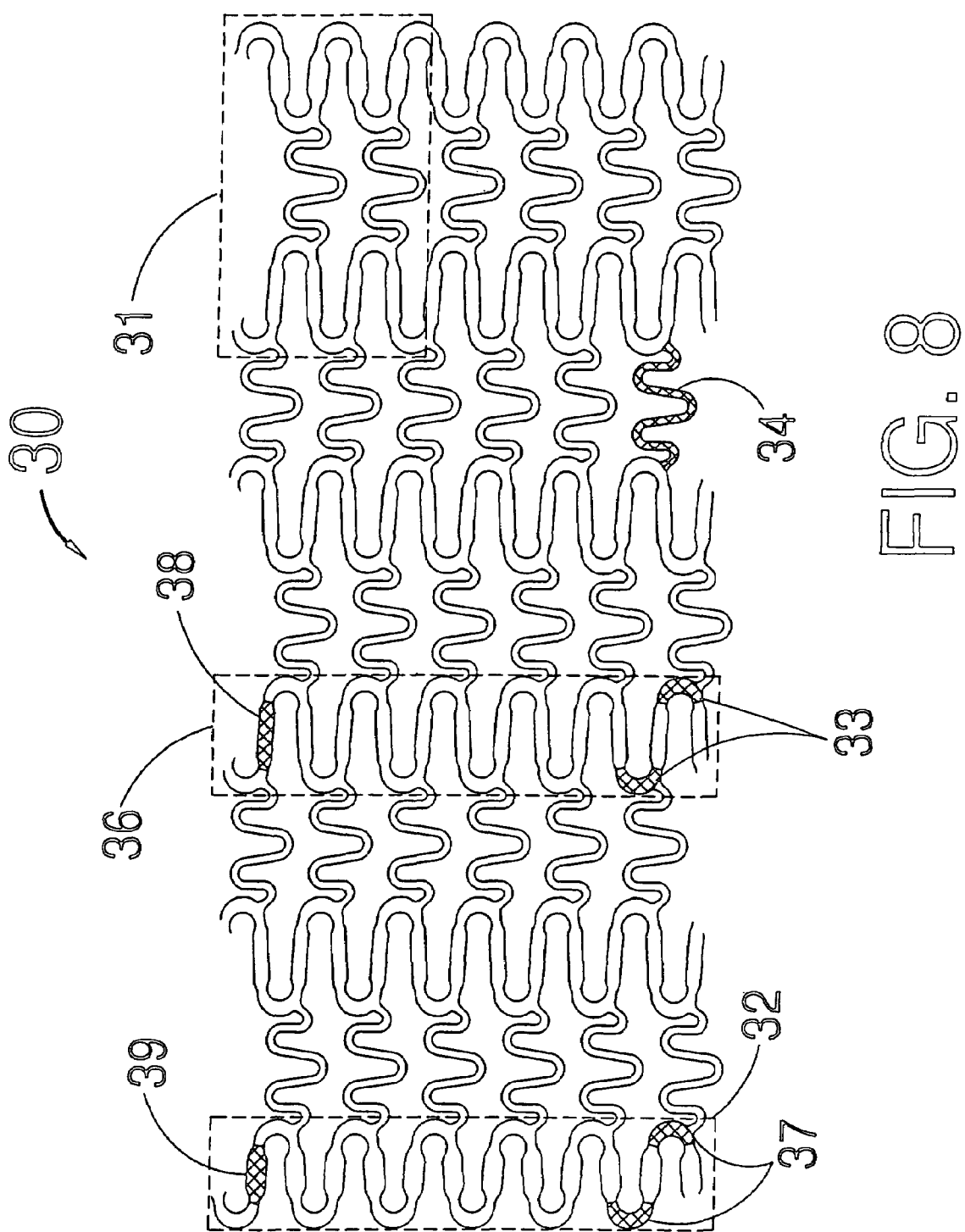
FIG. 8 is a flat layout of the present invention stent design for a somewhat radiopaque metal.

FIG. 8 is a flat layout view of another embodiment of the present invention showing a stent 30 made from a moderately radiopaque metal such as the cobalt-tungsten alloy L605. The alloy L605 has great radial strength and is approximately 20% to 30% more radiopaque than stainless steel. Therefore, with L605, the same level of radiopacity is achieved with a stent wall thickness that is 20% to 30% less than a stent made from stainless steel. One goal in the use of L605 would be to reduce the wall thickness by 30% but end up with a stent that is still more radiopaque than an equivalent stainless steel stent such as the stent 5 shown in FIG. 1.

The stent 30 of FIG. 8 is shown in a layout view based on its pre-deployed state, as it would appear before it is crimped onto a balloon catheter. The stent 30 comprises end sets of strut members 32 located at each end of the stent 30 and central sets of strut members 36 connected each to the other by sets of flexible "M" links 34. The "M" links 34 are similar to the "M" links 14 of FIG. 4. Each end set of strut members 32 comprises alternating curved sections 37 and diagonal sections 39 connected together to form a closed circumferential structure. The central sets of strut members 36 located longitudinally between the end sets of strut members 32 comprises curved sections 33 and diagonal sections 38 connected together to form a closed circumferential ring-like structure.

In the stent 30, the diagonal sections 39 of the end sets of strut members 32 are shorter in length than the diagonal sections 38 of the central sets of strut members 36. The shorter diagonal sections 39 will reduce the longitudinal length of metal at the end of the stent to improve deliverability into a vessel of the human body. In the stent 30, the widths of the diagonal sections 38 and 39 are different as compared to the prior art stents 5 and 60 of FIGS. 1 and 2.

Figure 9:
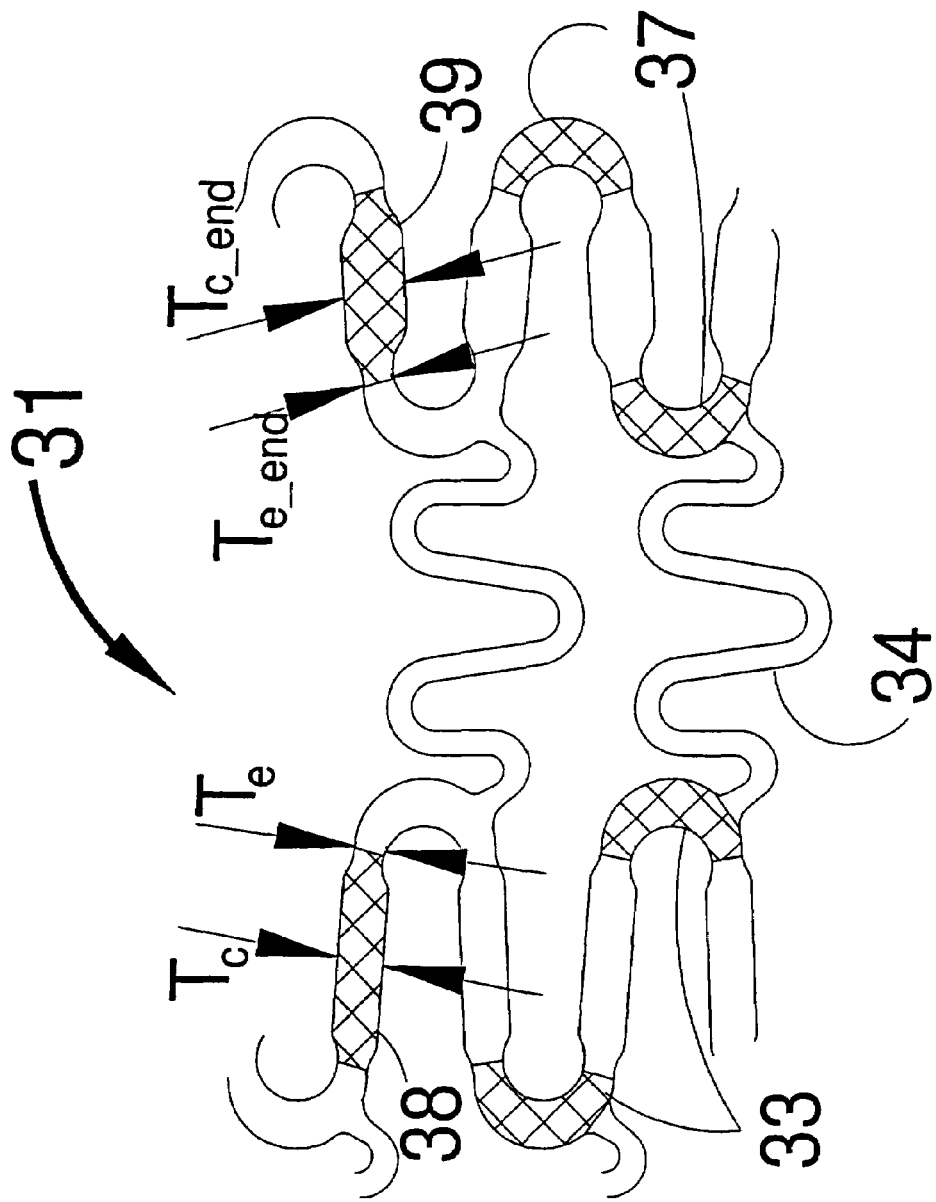
FIG. 9 is a flat layout of the present invention stent design for a stent coated with a radiopaque metal.

The novel concepts of the stent of FIG. 8 are shown most clearly in the expanded view of the stent section 31 shown in FIG. 9. In FIG. 9 it can be seen that the diagonal sections 38 of the central sets of strut members 36 have a width at the center $T_c$ and a width at the end $T_e$ where the width in the center $T_c$ is larger than the width at the end $T_e$. This allows for increased radiopacity without affecting the design of curved sections 33 that are the primary stent elements involved for stent expansion. The curved sections 33 and 37 shown in FIG. 9 are tapered similar to the curved sections 23 and 27 of FIG. 6. It is also envisioned that the curved sections 33 and 37 could have uniform width similar to the curved sections 3 and 7 of FIG. 1. The diagonal sections 39 of the end sets of strut members 32 also have a tapered shape. The diagonal sections 37 have a width in the center $T_{c\_end}$ and a width at the end $T_{e\_end}$ where the width in the center $T_{c\_end}$ is larger than the width at the end $T_{e\_end}$. Because of the desire for the end sets of strut members 32 to be the most radiopaque part of the stent 30, the diagonal section 39 center width $T_{c\_end}$ of the end sets of strut members 32 is shown in FIG. 9 to be wider than the width $T_c$ of the diagonal section 38. A wider piece of metal will be more radiopaque. Thus, the stent has curved sections with a single bend connecting the diagonal sections of its sets of strut members, and flexible connecting links connecting the curved sections of its circumferential sets of strut members.

Figure 10:
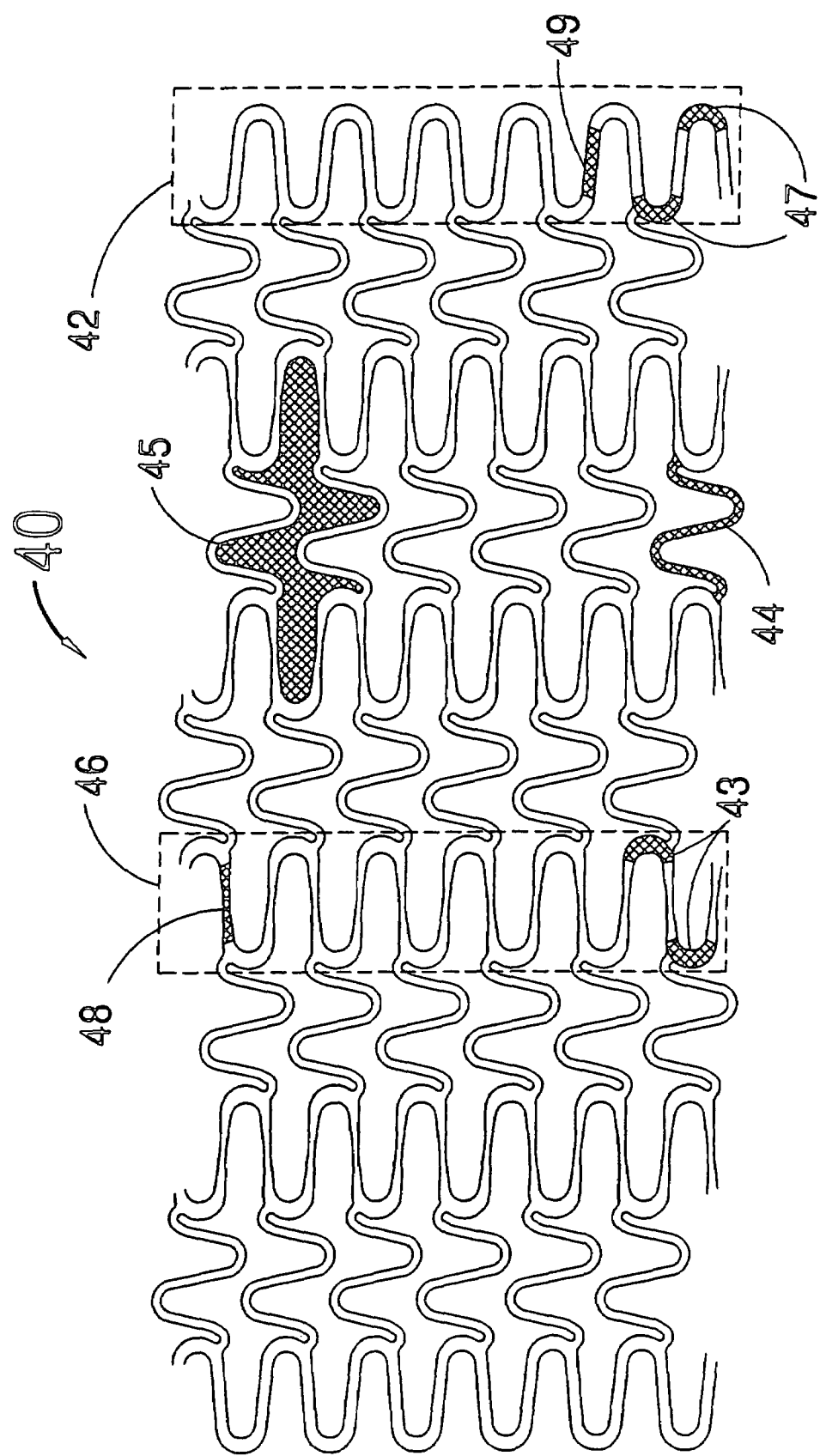
FIG. 10 is a flat layout of an alternate embodiment of the present invention stent including an "N" shaped flexible connecting link.

The stent of FIG. 10 is an alternate embodiment of the present invention showing central sets of strut members 46 having curved sections 43 and diagonal sections 48 with tapered shapes similar in design to the curved sections 23' and diagonal sections 28' of the stent section 21' shown in FIG. 7. The stent 40 of FIG. 10 is shown in a layout view in its pre-deployed state as it would appear before it is crimped onto a balloon catheter. The stent 40 comprises end sets of strut members 42 located at each end of the stent 40 and central sets of strut members 46. The sets of strut members 42 and 46 are connected each to the other by sets of individual flexible "N" links 44. The "N" links 44 are similar in shape but slightly longer than the "N" links 4 of FIG. 1. The end sets of strut members 42 consist of curved sections 47 and diagonal sections 49. The central sets of strut members 46 located longitudinally between the end sets of strut members 42 consist of curved sections 43 and diagonal sections 48.

The stent 40 is a closed cell stent having cells 45 formed from portions of adjacent sets of strut members connected by "N" links 44. Prolapse of plaque through the closed cells 45 is minimized if the expanded area of the cell 45 is less than about 0.005 in.$^2$ at any diameter up to the maximum deployment diameter of the stent 40. It is also important for an optimum stent design that a guidewire can be placed through the expanded cell 45 into a side branch vessel. A balloon angioplasty catheter would then be advanced over the guidewire, through the cell 45 and inflated to "unjail" the side branch, i.e. remove any stent strut that is blocking blood flow into that side branch. The present invention design should have an interior perimeter of the cell 45 that is at least 9 mm, thus allowing a nearly 3 mm diameter circular opening to be achieved for unjailing.

Figure 11:
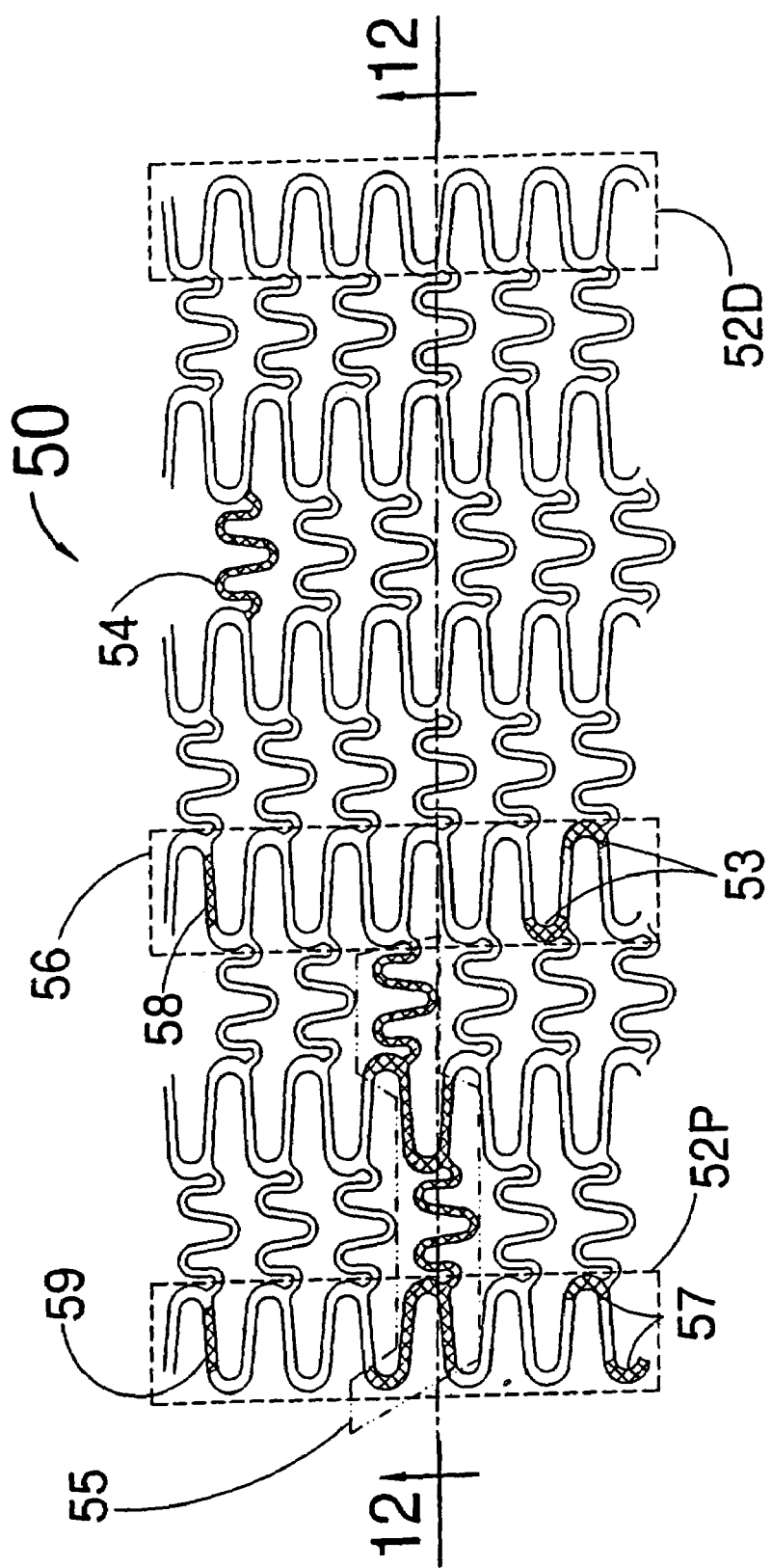
FIG. 11 is a flat layout of the present invention stent design as photo-etched from a tube.

FIG. 11 is a flat layout view of another embodiment of the present invention in the form of a stent 50 that is photo-etched from a metal tube. The stent 50 is shown in its pre-deployed state as it would appear before it is crimped onto a balloon catheter. The stent 50 comprises end sets of strut members 52P and 52D located respectively at the proximal and distal ends of the stent 50. The stent 50 also has central sets of strut members 56 connected each to the other by sets of flexible "M" links 54. The "M" links 54 are similar to the "M" links 14 of FIG. 4. The end sets of strut members 52P and 52D each consists of curved sections 57 and diagonal sections 59. The central sets of strut members 56 located longitudinally between the end sets of strut members 52 consist of curved sections 53 and diagonal sections 58.

Figure 12A:
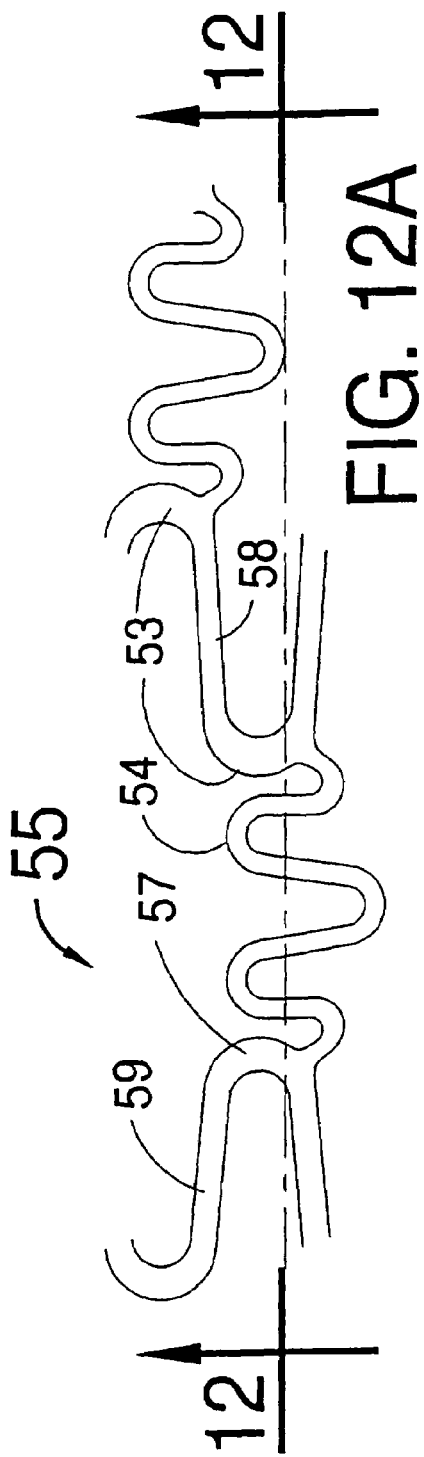
FIG. 12A is an enlargement of a section of the photo-etched stent of FIG. 11.

The section 55 of the photo-etched stent 50 is shown enlarged in FIG. 12A. The FIGS. 12B and 12C show two embodiments of the present invention that can provide a stent with enhanced radiopacity at the stent ends.

FIG. 12A shows diagonal sections 58 and 59 and an "M" link 54 connecting the curved sections 53 and 57.

Figure 12B:
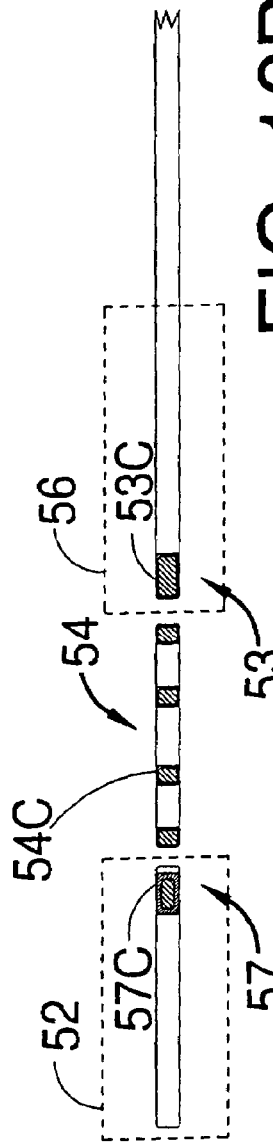
FIG. 12B is a longitudinal cross section at 12-12 of the enlarged section of FIG. 11 shown in FIG. 12A, the stent having a radiopaque coating that is thickest on the end sets of strut members.
Figure 12C:
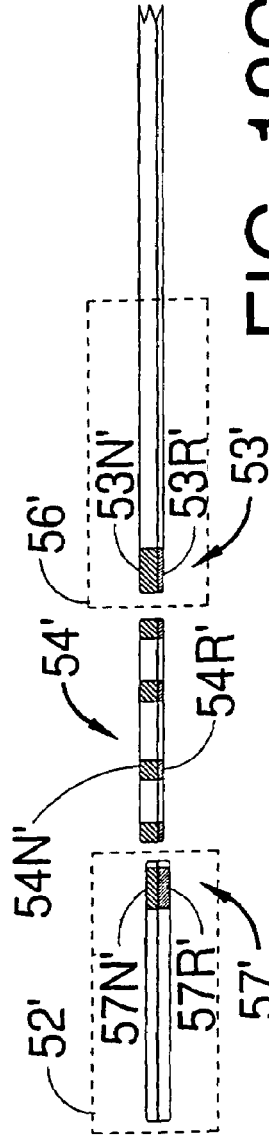
FIG. 12C is a longitudinal cross section at 12-12 of the enlarged section of FIG. 11 shown in FIG. 12A, as etched from a two-layer tube where one of the tube layers is a moderately radiopaque metal and the other layer is a highly radiopaque metal.

FIG. 12B is a longitudinal cross section at 12-12 of the stent section 55 shown in FIG. 12A. The stent design shown in FIG. 12B has a highly radiopaque coating that is thicker on the end sets of strut members 52 as compared to the thickness on either the flex links 54 or the central sets of strut members 56. FIG. 12B shows the coating 57C on the curved section 57 of the end set of strut members 52 being thicker than the coating 54C on the flex link 54 and also thicker than the coating 53C on the curved section 53. The most likely coating for the stent 50 would be gold plating although platinum, tantalum or any other highly radiopaque metal could be used.

The present invention has the entire stent coated to provide an exterior surface for the stent 50 that is formed from a single metal. This reduces the potential for corrosion that can occur with dissimilar metals on the stent's exterior surface when the stent is placed in a saline solution such as blood.

It is also envisioned that even with the entire stent coated with a highly radiopaque metal, an additional coating of a flexible plastic such as parylene may be desirable. Such an organic coating has the additional advantage of allowing the attachment of drugs such as taxol or rapamycin to reduce restenosis. Techniques for gold plating metals such as stainless steel and controlling the thickness of the plating are well known in the art of metal plating.

FIG. 12C is the longitudinal cross section at 12-12 of yet another alternate embodiment of the enlarged section 55 of FIG. 11 shown in FIG. 12A. The stent design shown in FIG. 12C is etched from a two-layer tube where one of the tube layers is a metal of conventional radiopacity such as stainless steel and the other layer is a highly radiopaque metal such as tantalum. Although the total wall thickness of the stent of this embodiment remains nearly constant, the end sets of strut members 52' have a thicker layer of the radiopaque metal than the flex links 54' or the central sets of strut members 56'. The curved section 57' of the end set of strut members 52' has conventional metal layer 57N' and radiopaque metal layer 57R'. The flex link 54' has a standard metal layer 54N' and a radiopaque metal layer 54R'. The central sets of strut members 56' have curved sections 53' with conventional metal layers 53N' and radiopaque metal layers 53R'.

It can be seen from FIG. 12C that the radiopaque metal layer 57R' of the end sets of strut members 52' is thicker than the radiopaque metal layers 54R' and 53R'. In recent years, multi-layer photo-etching processes for metals that can control the thickness of individual layers have been developed so that the embodiment of FIG. 12C can be produced within the current state of the art of photo-etching. Using this approach, two and three layer tubing is now available from several manufacturers and can be photo-etched to make a stent with an optimal design which is high radiopacity for the end set of strut members and reduced radiopacity for the central sets of strut members. Specifically, a stent with the characteristics as seen in FIG. 12B or FIG. 12C would have the desirable attribute of end sets of strut members with greater radiopacity than the remainder of the stent.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A stent in the form of a thin-walled, multi-cellular, tubular structure having a longitudinal axis, the stent comprising a multiplicity of circumferential sets of strut members, each set of strut members being longitudinally separated each from the other and connected each to the other by one or more longitudinally extending links, each set of strut members forming a closed, cylindrical portion of the stent, each set of strut members comprising a multiplicity of connected curved sections and diagonal sections, the sets of strut members including end sets of strut members located at each end of the stent and central sets of strut members positioned between the end sets of strut members, each of the sets of strut members being coated with a highly radiopaque metal, the end sets of strut members having a greater wall thickness of the highly radiopaque coating as compared to a lesser thickness of the radiopaque coating on the central sets of strut members so as to have an increased radiopacity of the end sets of strut members.

2. The stent of claim 1 wherein the highly radiopaque metal is gold.

3. The stent of claim 1 wherein the highly radiopaque metal is coated with a plastic material.

4. The stent of claim 3 wherein the plastic coating is parylene.

* * * * *